United States Patent
Gomez et al.

(10) Patent No.: US 11,013,574 B1
(45) Date of Patent: May 25, 2021

(54) MOUNTING TELEOPERATED SURGICAL ARMS

(71) Applicant: Intuitive Surgical Operations, Inc., Sunnyvale, CA (US)

(72) Inventors: Daniel H. Gomez, Los Gatos, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 35 days.

(21) Appl. No.: 16/408,077

(22) Filed: May 9, 2019

Related U.S. Application Data

(60) Provisional application No. 62/669,687, filed on May 10, 2018.

(51) Int. Cl.
*A61B 17/02* (2006.01)
*A61B 90/50* (2016.01)
(Continued)

(52) U.S. Cl.
CPC ........ *A61B 90/50* (2016.02); *A61B 17/00234* (2013.01); *A61B 34/35* (2016.02); *A61B 46/10* (2016.02); *A61B 50/10* (2016.02); *A61B 2090/571* (2016.02); *A61G 13/02* (2013.01); *A61G 13/101* (2013.01)

(58) Field of Classification Search
CPC ....... A61B 90/50; A61B 90/361; A61B 34/35; A61B 34/71; A61B 34/30; A61B 34/20; A61B 17/00234; A61B 46/10; A61B 50/50; A61B 19/00; A61B 2090/571; A61B 2017/00261; A61B 2034/2061; A61B 2034/102; A61B 2034/2051; A61G 13/01; A61G 13/10; A61G 13/101; A61G 13/12;
(Continued)

(56) References Cited

U.S. PATENT DOCUMENTS 5,704,900 A * 1/1998 Dobrovolny ....... A61B 17/0281
600/227
6,120,433 A * 9/2000 Mizuno .................. A61B 34/70
600/102
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
(Continued)

*Primary Examiner* — Pedro Philogene
(74) *Attorney, Agent, or Firm* — Fish & Richardson P.C.

(57) ABSTRACT

A medical device system includes: a surgical arm mounting device including a coupler and a surgical arm interface, the coupler including a clamp for a first side rail of an operating table; and a support member including a brace, the brace extending from the coupler at least part way across the width of an operating table. The clamp has a first mechanical state in which the mounting device is fixed to the side rail, a second mechanical state in which the mounting device is translatable along the side rail, and a third mechanical state in which the mounting device is removable from the side rail. The surgical arm interface is configured to receive a mating mounting device interface of a surgical arm.

19 Claims, 6 Drawing Sheets

(51) Int. Cl.
  *A61B 34/35* (2016.01)
  *A61B 17/00* (2006.01)
  *A61B 46/10* (2016.01)
  *A61B 50/10* (2016.01)
  *A61G 13/02* (2006.01)
  *A61G 13/10* (2006.01)
  *A61B 90/57* (2016.01)

(58) Field of Classification Search
  CPC ......... A61G 7/0503; A47B 41/04; F16B 2/18; B25J 5/02
  USPC ............ 606/130, 1; 600/101, 102, 118, 117, 600/201–235; 395/92, 99, 85; 901/2, 47; 709/208; 248/231.85

See application file for complete search history.

(56) References Cited

U.S. PATENT DOCUMENTS

| | | | |
|---|---|---|---|
| 6,210,323 B1* | 4/2001 | Gilhuly | A61B 17/02 600/208 |
| 6,409,735 B1 | 6/2002 | Andre et al. | |
| 10,363,190 B2* | 7/2019 | Elias | A61G 13/1235 |
| 10,500,739 B2* | 12/2019 | Auld | A61B 34/30 |
| 2003/0205176 A1 | 11/2003 | Kolody et al. | |
| 2008/0034502 A1 | 2/2008 | Copeland et al. | |
| 2012/0241576 A1* | 9/2012 | Yu | A61B 34/71 248/231.85 |
| 2016/0136028 A1 | 5/2016 | Koch et al. | |

OTHER PUBLICATIONS

International Preliminary Report on Patentability for Application No. PCT/US2019/029293, dated Nov. 19, 2020, 8 pages.
International Search Report and Written Opinion for Application No. PCT/US2019/029293, dated Aug. 8, 2019, 10 pages.

* cited by examiner

MOUNTING TELEOPERATED SURGICAL ARMS

CLAIM OF PRIORITY

This application claims priority to U.S. Provisional Patent Application No. 62/669,687 filed on May 10, 2018, the entire contents of which are hereby incorporated by reference.

TECHNICAL FIELD

This specification generally relates to teleoperated surgical systems and, more specifically, to techniques for mounting teleoperated surgical arms.

BACKGROUND

Minimally invasive medical techniques (e.g., laparoscopy) have been used to reduce the amount of extraneous tissue damaged during diagnostic or surgical procedures, thereby reducing patient recovery time, discomfort, and harmful side effects. Such techniques were traditionally performed manually via a surgeon manipulating various surgical instruments within the patient's body but can now be implemented using computer-assisted teleoperated systems. The use of minimally invasive teleoperated surgical systems facilitates increased precision and range of motion in manipulating surgical instruments when compared to manual techniques, but it also introduces new challenges. These systems move components that have significant mass, and so operating challenges include limited movability, portability, flexibility during set up for a surgical procedure, as well as velocity and stability considerations while operating a system during the procedure. System cost is also a consideration, because reducing costs benefits patients and hospitals. Likewise system size and complexity are considerations because smaller operating rooms may not be able to accommodate the major surgical system components. Improvements for set-up and operation of such systems are continuously sought.

SUMMARY

A modular surgical system architecture has many benefits. In a modular system architecture, only the components needed for each procedure are used. After the procedure, the system can be disassembled and its components individually stored when not used. For example, if a procedure requires only three teleoperated surgical arms, only those three arms are removed from a storage location and used during a surgical procedure. After the procedure, the arms are cleaned as necessary and then stored for the next use, which may require a different number of arms. In some instances only a single arm may be required, such as to support, move, and operate an endoscopic imaging device or a therapeutic end effector such as a stapler. Surgeons can use a combination of manual and teleoperated surgical instruments to perform a procedure. Therefore, a modular surgical system architecture offers the benefits of relatively lower cost and smaller size than full surgical systems.

A teleoperated surgical arm can be mounted on an individual cart that can be moved in the operating room with reference to the patient. Alternatively, a teleoperated surgical arm may be mounted to the operating table.

Various operating table designs exist. Operating tables typically include rails on each side. Equipment required during surgery can be secured to the rails. Although relatively strong and stiff, the rails may not provide the necessary stiffness necessary to minimize vibration in a teleoperated surgical arm attached to the rail. Improved techniques for mounting a teleoperated manipulator arm to an operating table are needed.

Accordingly, a first aspect of the present disclosure includes a medical device system including: a surgical arm mounting device including a coupler and a surgical arm interface, the coupler including a clamp for a first side rail of an operating table; and a support member including a brace, the brace extending from the coupler at least part way across the width of an operating table. The clamp has a first mechanical state in which the mounting device is fixed to the side rail, a second mechanical state in which the mounting device is translatable along the side rail, and a third mechanical state in which the mounting device is removable from the side rail. The surgical arm interface is configured to receive a mating mounting device interface of a surgical arm.

In some examples, the system further includes a second mounting device including a second coupler, and the second coupler includes a second clamp for a second side rail of the operating table opposite the first side rail. In some examples, the second clamp has a first mechanical state in which the mounting device is fixed to the second side rail, a second mechanical state in which the mounting device is translatable along the second side rail, and a third mechanical state in which the second mounting device is removable from the second side rail. In some examples, the second mounting device includes a second surgical arm interface, and the second surgical arm interface is configured to receive the mating mounting device interface of the surgical arm.

In some examples, in the first mechanical state, the clamp is fixed to the side rail through a surgical drape, and in the second mechanical state, the clamp is translatable along the side rail over the surgical drape.

In some examples, the brace extends over a top surface of the operating table.

In some examples, the brace includes a broad, flat body.

In some examples, the brace extends underneath the operating table.

In some examples, the mounting device further includes first and second ports for a transportable medium and a conduit for the transportable medium extending between the first and second ports. In some examples, the conduit extends from the first port to the second port through the interior of the mounting device. In some examples, the conduit includes at least one of a fluid conduit or an electrical conduit.

In some examples, the system further includes the operating table. In some examples, the system further includes the surgical arm. In some examples, the system further includes a surgical drape between a side rail of the table and the clamp.

A second aspect of the present disclosure includes a teleoperated surgical arm mounting system including: means for releasably coupling to a first side rail of an operating table; means for bracing the means for releasably coupling against a second part of the operating table; and means for mating a teleoperated surgical arm to the means for releasably coupling.

In some examples, the second part of the operating table includes a second side rail on an opposite side of the operating table. In some examples, the second part of the operating table includes the bottom of the table. In some examples, the second part of the operating table includes the top of the table. In some examples, the second part of the operating table includes a side of the table. In some examples, the means for releasably coupling includes means for releasably coupling over a surgical drape covering the first side rail.

A third aspect of the present disclosure includes a method of setting up a teleoperated surgical system to perform a surgical procedure, the method including the steps of: releasably coupling a coupling device to a first position on a side rail of an operating table; bracing the coupling device against a first position of the operating table other than the first position on the side rail; and mating a teleoperated surgical arm to the coupling device.

In some examples, the method further includes the steps of: releasing the coupling device from the first position; releasing the bracing from the first position; translating the coupling device along the side rail to a second position on the side rail; releasably clamping the coupling device to the second position on the side rail; and bracing the coupling device to a second position of the operating table other than the second position on the side rail.

In some examples, releasing the coupling device from the first position includes releasing the coupling device from a surgical drape covering the side rail.

In some examples, translating the coupling device along the side rail to the second position includes translating the coupling device over the surgical drape.

In some examples, releasably clamping the coupling device to the second position on the side rail includes clamping the coupling device to the side rail over the surgical drape.

A fourth aspect of the present disclosure includes a method of setting up a teleoperated surgical system to perform a surgical procedure, the method including the steps of: coupling a mounting device to a first portion of the operating table; connecting a teleoperated surgical arm to a surgical arm interface of the mounting device; connecting a first end of a brace to the mounting device; and coupling a second end of the brace to a second portion of the operating table.

A fifth aspect of the present disclosure includes a medical device system including: an auxiliary rail including a frame and a flange extending from the frame; and a surgical arm mounting device including a coupler and a surgical arm interface. The frame is configured to be mounted on a side rail of an operating table. The coupler includes a clamp for the flange of the auxiliary table rail. The clamp of the coupler has a first mechanical state in which the mounting device is fixed to the auxiliary rail and a second mechanical state in which the mounting device is translatable along the auxiliary rail. The surgical arm interface receives a mating mounting device interface of a surgical arm.

In some examples, the frame includes a clamp for the side rail of the operating table, the clamp of the frame being separate from the clamp of the coupler. In some examples, the clamp of the coupler has a first mechanical state in which the auxiliary rail is fixed to the side rail of the operating table and a second mechanical state in which the auxiliary rail is removable from the side rail.

In some examples, the system further includes a brace extending from the auxiliary rail at least part way across the width of the operating table.

In some examples, the auxiliary rail includes a first auxiliary rail, and the system further includes a second auxiliary rail including a second frame and a second flange extending from the second frame, the second frame configured to be mounted on a second side rail of the operating table. In some examples, the system further includes a brace coupling the first and second auxiliary rails. In some examples, the brace extends along at least a portion of the operating table.

In some examples, the stiffness of the auxiliary rail is greater than the stiffness of the side rail of the operating table.

In some examples, when the clamp of the auxiliary rail is in the first mechanical state, the frame of the auxiliary rail is adjacent to a portion of the operating table, such that a load associated with the surgical arm causes the operating table to exert a reactionary force against the frame.

In some examples, the system further includes the operating table. In some examples, the system further includes the surgical arm.

In some examples, in the first mechanical state, the clamp of the coupler is fixed to the auxiliary rail through a surgical drape; and in the second mechanical state, the clamp is translatable along the auxiliary rail over the surgical drape.

In some examples, the mounting device further includes first and second ports for a transportable medium and a conduit for the transportable medium extending between the first and second ports. In some examples, the conduit extends from the first port to the second port through the interior of the mounting device. In some examples, the conduit includes at least one of a fluid conduit or an electrical conduit.

A sixth aspect of the present disclosure includes a method for mounting a teleoperated surgical arm to an operating table, the method including the steps of: releasably coupling a frame of an auxiliary rail to a side rail of an operating table; releasably coupling a mounting device to a flange extending from the frame of the auxiliary rail; and mating a teleoperated surgical arm to the mounting device.

In some examples, releasably coupling the frame of an auxiliary rail to a side rail of an operating table includes the steps of: sliding the frame along the length of the side rail; and clamping the frame against the side rail.

In some examples, releasably coupling the frame of the auxiliary rail to a side rail of an operating table includes the step of bracing the frame against at least one other portion of the operating table.

In some examples, the auxiliary rail includes a first auxiliary rail, and the method further includes the step of releasably coupling a second frame of a second auxiliary rail to a second side rail of the operating table simultaneously with the first auxiliary rail. In some examples, the method further includes the step of releasably coupling a brace supporting the first and secondary auxiliary rails to the operating table simultaneously with releasably coupling the first and second auxiliary rails to the side rails of the operating table. In some examples, simultaneously coupling the brace and first and second auxiliary rails to the operating table includes the step of sliding the brace and first and second auxiliary rails onto the operating table as an assembled modular unit.

In some examples, the method further includes the steps of: releasing the mounting device from the flange extending from the frame of the auxiliary rail; repositioning the mounting device along the auxiliary rail; and re-coupling the mounting device to the flange.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings may indicate like elements.

DETAILED DESCRIPTION

Embodiments of the present disclosure relate to technology (e.g., systems, apparatus, devices, and methods) for mounting a kinematic surgical arm that includes a teleoperated surgical manipulator (a surgical arm) to an operating table. In particular, certain mounting systems described throughout this disclosure are appropriately configured to retrofit a conventional operating table in a manner that provides a robust and stable mounting point for securing a teleoperated surgical arm to the table.

Continued development of teleoperated surgical systems has led to the implementation of individual surgical arms that can be received and supported by a relatively compact interface. The interface can be a part of a portable module positionable near a patient's body and secured to an operating room structure (e.g., an operating table) by medical staff prior to a surgical procedure. This modular configuration provides an alternative to other arrangements where one or more surgical arms are attached to a comparatively large support assembly on a stand-alone structure. Accordingly, one advantage that may be gained from implementing the more compact modular system is more efficient space utilization in an operating room.

Various embodiments described within this disclosure are derived from a realization that many existing operating tables were not designed to support a teleoperated surgical arm. Though many operating tables have side rails, these rails are typically designed for mounting the relatively lightweight instruments and/or accessories used by surgeons during traditional manual surgical procedures. Nevertheless, it may be desirable and advantageous to use the operating table's side rails for mounting a teleoperated robotic surgical arm for multiple reasons. First, the rails are conveniently located on a side of the operating table, and therefore proximate the target location of the surgical arm—i.e., near the patient. Second, the side rails allow a variety of objects to be readily attached to the operating table by clamps (or other similar coupling devices).

Accordingly, the present disclosure describes various mounting systems that can be attached to an operating table in a manner that adds stability to the standard side rails, offering a robust and sturdy mounting point to secure a surgical arm during a surgical procedure. Employing the mounting systems described below enables the use of surgical arms with pre-existing operating tables, which allows a medical facility to obtain the benefits of teleoperated minimally invasive surgery at lower cost.

Figure 1:
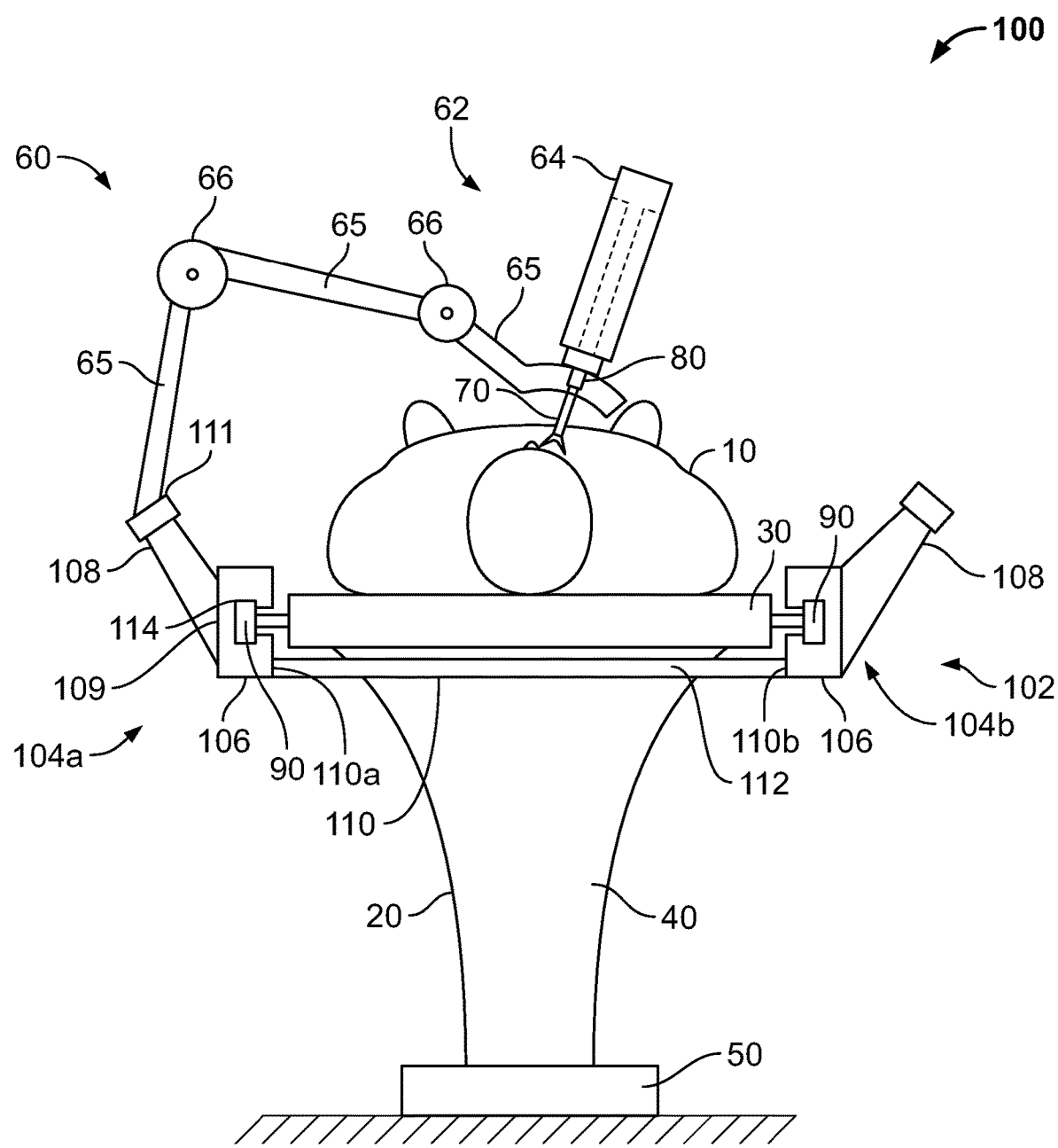
FIG. 1 is a front view of a first example mounting system securing a teleoperated surgical arm to an operating table.

FIG. 1 is a schematic view that depicts a teleoperated surgical manipulator system 100 of a teleoperated surgical system in accordance with one or more embodiments of the present disclosure. Manipulator system 100 is a teleoperated system for performing minimally invasive surgery on a patient's body 10 positioned on an operating table 20.

Operating table 20 includes a tabletop 30 on which the patient's body 10 is placed, a vertically extending pillar 40 that supports tabletop 30, a base 50 supporting pillar 40 and tabletop 30 on a floor surface, and side rails 90. Operating table 20 can be provided in the form of any structure suitable for supporting a patient during a medical procedure. Suitable structures include, but are not limited to, a general surgery table, an imaging table, a neurology table, an obstetric table, a military operating table, and other similar structures. Tabletop 30 is depicted in FIG. 1 as a monolithic and substantially planar structure, but other tabletop configurations are also contemplated within the scope of this disclosure. For example, the tabletop could be a multi-component apparatus with independently articulating sections that enable adjustment of the patient's body position (see, e.g., FIG. 6). Further, while tabletop 30 is depicted in a horizontal orientation normal to the vertically extending pillar 40 and parallel to the floor surface on which base 50 is grounded, other configurations and arrangements are also contemplated. For example, tabletop 30 could be mounted at a non-perpendicular angle relative to pillar 40, such that either the upper or lower portion of the patient's body 10 is elevated, or the tabletop could be adjustably mounted to pillar 40 to enable a variety of orientations. Similarly, though FIG. 1 shows a base 50 statically grounded to a floor surface and a single, centrally located pillar 40, other suitable operating tables could have a horizontally extending pillar, a wheeled base, a base designed to slide along a track or rail, and/or a multi-legged support system.

Side rails 90 are elongated structures that extend lengthwise along operating table 20. In this example, side rails 90 have a rectangular cross section and are spaced apart from the table by supports that project laterally outward from tabletop 30. Other suitable rail configurations and arrangements are also contemplated. For example, side rails suitable for use with techniques of the present disclosure may continuously extend laterally along the table or portion of the table, or they may have cross sections with a bullhead shape, a "C" shape, or any other shape that enables a removable clamp to be secured to the rail.

Manipulator system 100 further includes a surgical arm 60 and a surgical arm mounting system 102. Surgical arm 60 includes an instrument manipulator 62, and manipulator 62 includes an instrument carriage 64 at a distal end of instrument manipulator 62. Instrument carriage 64 supports a detachable surgical instrument 70. Instrument manipulator 62 is teleoperated and controls positioning of surgical instrument 70 relative to the patient's body 10. In various implementations, instrument manipulator 62 may be provided in a variety of forms that allow surgical instrument 70 to move with one or more mechanical degrees of freedom (e.g., all six Cartesian degrees of freedom, five or fewer Cartesian degrees of freedom, etc.). Typically, mechanical or control constraints restrict instrument manipulator 62 to move surgical instrument 70 around a defined center of motion that remains stationary with reference to the patient's body 10. This center of motion is typically located at or near where surgical instrument 70 enters the patient's body 10. One or more optional proximal links 65 may function as a setup arm portion of the surgical arm, which holds the manipulator portion at a fixed pose in space during surgery. Setup arms may be manually moved or teleoperated, powered or unpowered. Persons of skill in the art will be familiar with various surgical arm, manipulator, and setup arm designs. Examples of surgical arms that include manipulator and setup portions are disclosed in Int'l. Publication Nos. WO 2018/053305 A1 (filed Sep. 15, 2017) and WO 2018/075527 A1 (filed Oct. 17, 2017), both incorporated herein by reference. Other examples are illustrated by the da Vinci Si® and da Vinci Xi® Surgical Systems commercialized by Intuitive Surgical, Inc., Sunnyvale, Calif. In the examples, surgical arm 60 has a mass on the order of 5 to 15 Kg, although the mass may be more or less depending on the arm design. If the arm itself can be disassembled, that mass of its individual components will be less. This relatively low mass allows a clinical worker to easily carry and set up the arm for surgery.

FIG. 1 further depicts a first example surgical arm mounting system 102 that includes first and second mounting devices 104a,104b and a support member 110 that extends between mounting devices 104a,104b. As shown, mounting devices 104a,104b are each secured to one of the side rails 90 on either side of operating table 20, and support member 110 extends under tabletop 30 (e.g., along the bottom of the operating table). Each mounting device 104a,104b includes a coupler 106 and a surgical arm interface 108. Coupler 106 is configured (e.g., functionally designed and sized) to releasably secure mounting device 104 onto side rail 90 in a fixed position. In the example of FIG. 1, coupler 106 includes a clamp 114 for this purpose. As further discussed below with respect to FIGS. 2-3, clamp 114 can be operated in a manner that transitions coupler 106 between a locked state and an unlocked state, which enables selective movement of mounting device 104 along side rail 90 for adjusting the location of surgical arm 60 relative to the patient's body 10. As shown, mounting system 102 is optionally reversible so that the positions of mounting devices 104a,104b are reversed. In an optional implementation, the surgical arm interface 108 may be eliminated from mounting device 104b so that mounting system 102 includes only a single arm interface 108. Mounting system 102 is another component in a modular teleoperated surgical system, and in various embodiments its weight is low enough to allow a single clinician to install it to the table.

Surgical arm interface 108 is fixed to coupler 106. In example implementations, these components are integrally formed as a monolithic structure, or they are formed separately and subsequently attached via mechanical fasteners (e.g., bolts) or fusing processes (e.g., welding). Surgical arm interface 108 projects from a first end 109 at coupler 106 to a second end 111. The proximal end of surgical arm 60 is mated to second end 111. The body of surgical arm interface 108 between the first and second ends 109,111 provides sufficient strength and stiffness to bear the weight of surgical arm 60 during a surgical procedure. The mated connection between surgical arm interface 108 and surgical arm 60 at second end 111 couples arm 60 to mounting device 104, and therefore surgical arm 60 is coupled to side rail 90 of operating table 20 via coupler 106. As discussed below, in some examples surgical arm interface 108 optionally includes one or more ports at second end 111 for communicating a transportable medium (e.g., power, electrical or optical control signals, liquid, or gas) to and/or from surgical arm 60.

Support member 110 is a rigid connection between mounting devices 104a,104b. In this example, the combination of support member 110 and mounting devices 104a, 104b provides a single rigid body that is coupled to operating table 20. Support member 110 has a first end 110a connected to first mounting device 104a and a second end 110b connected to second mounting device 104b. Each of the two mounting devices 104a,104b are removable secured to a side rail 90 of operating table 20 by clamp 114 of coupler 106. The connections between the support member's ends 110a,110b and mounting devices 104a,104b can be established by any suitable permanent or reversible manner. For example, the connections can be made by mechanical fasteners, adhesives, fusing, welding, etc.

Support member 110 includes a brace 112 (e.g., a rod, a shaft, or plate, etc.; optionally a single link or two or more links rigidly coupled together) that extends horizontally between the two ends 110a,110b of support member 110. In this example, brace 112 is below tabletop 30, positioned vertically between tabletop 30 and base 50 of operating table 20, when mounting system 102 is coupled to table 20. Brace 112 reinforces the operating table's side rails 90 by accepting a portion of the mechanical load of surgical arm 60 through the mounting devices 104. This load sharing effect reduces the amount of bending/twisting stress on the cantilevered side rail 90 nearest surgical arm 60, and therefore it lessens dynamic bending/twisting and associated vibration in arm 60, and even the risk of failure of the connection between arm 60 and a side rail 90. The reinforcement provided by brace 112 also reduces, and in some examples practically or completely eliminates, deflection of side rail 90 that may be caused by the static and dynamic loads (e.g., weight, force from teleoperated motion) of surgical arm 60. In other words, the combination of side rail 90 and mounting system 102 provides a support system for surgical arm 60 with stiffness that is higher than if surgical arm 60 is connected to only a single side rail 90. The reduction in deflection results in a substantial reduction of vibration that would otherwise be caused by the dynamic load of surgical arm 60 as the arm moves during a surgical procedure. As previously discussed, relative movement between surgical arm 60 and operating table 20 could detrimentally affect the ability of surgical arm 60 to effectively execute a surgical procedure. The degree of reinforcement provided by brace 112 may vary across different implementations depending on a variety of factors, including its strength and stiffness. These characteristics are a function of the material and/or geometry of brace 112, as well as of mounting system 102 as a whole.

Figure 2:
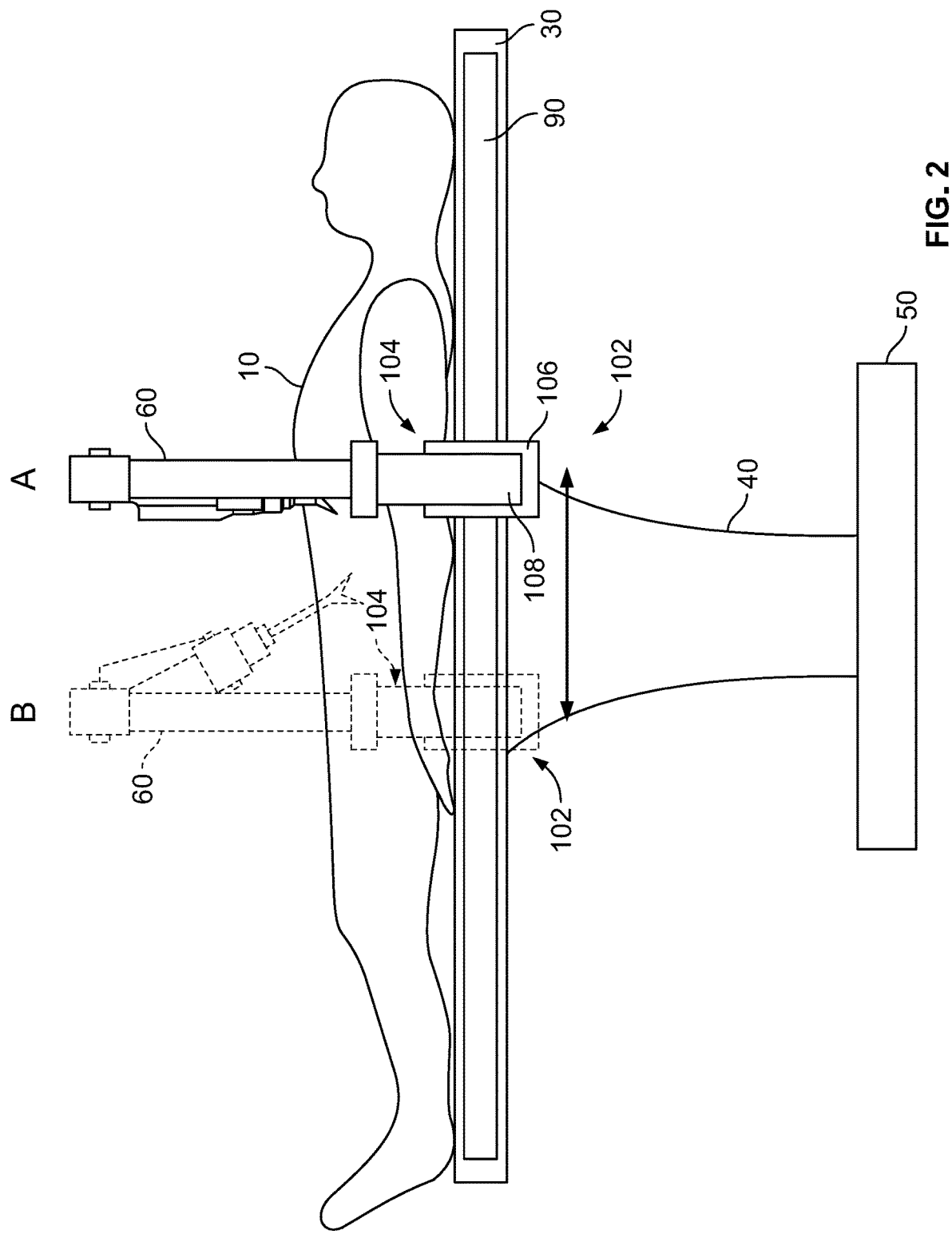
FIG. 2 is a side view of the first example mounting system and operating table.
Figure 3:
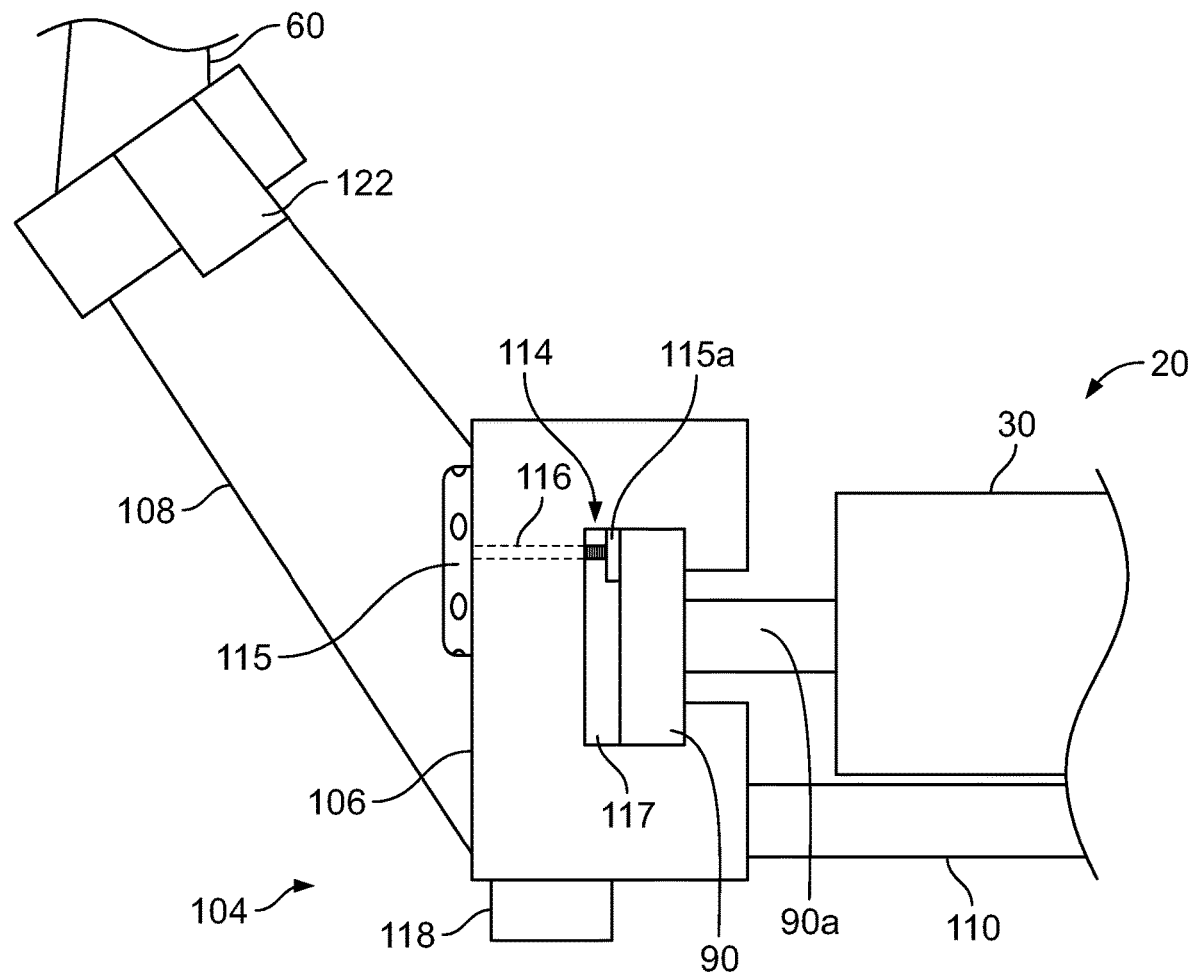
FIG. 3 is an enlarged view of a portion of the first example mounting system.

FIG. 2 is a schematic side view that shows an example surgical arm mounted to an operating table using mounting system 102. FIG. 2 illustrates how mounting device 104 is movable along side rail 90 of operating table 20 to adjust the position of surgical arm 60 relative to the patient's body 10. Movement of mounting device 104 can be accomplished by sliding coupler 106 along side rail 90. Optionally, mounting device 104 may be moved by disengaging coupler 106 from side rail 90, moving mounting device 104 to a desired position, and then re-engaging coupler 106 with side rail 90. One advantage gained by sliding coupler 106 along side rail 90 is that repositioning can be performed while surgical arm 60 remains attached to mounting device 104, thus simplifying the surgical set-up process. An example of the mating cross-sectional shapes of coupler 106 and side rail 90 that enable the sliding motion are depicted in FIG. 3. As previously discussed, a clamp 114 (see FIGS. 1 and 3) enables coupler 106 to transition between a locked state, in which mounting device 104 is secured to side rail 90 in a fixed position, and an unlocked state, in which mounting device 104 remains attached to side rail 90 but is able to translate by sliding coupler 106 along side rail 90. The dashed outline of components and the double-headed arrow in FIG. 2 illustrate how, when coupler 106 is in the unlocked state, mounting device 104 and the attached surgical arm 60 can be moved from a first position (Position A) to a second position (Position B) along the operating table's side rail 90.

FIG. 3 is a schematic view that illustrates mounting device 104 secured to side rail 90 with coupler 106 placed in a locked state via clamp 114. In this example, coupler 106 has a "C"-shaped cross section configured (e.g., appropriately sized and shaped) to receive side rail 90 in a manner that facilitates the sliding motion of coupler 106 previously discussed with reference to FIG. 2. The "C" shape also allows mounting device 104 to slide past spacers 90a that couple side rail 90 to table 20. Illustrative clamp 114 is a C-clamp formed by the C-shaped frame of coupler 106 and a threaded shaft 115 that projects through a threaded bore 116 and into a cavity 117 defined by the C-shaped frame that receives side rail 90. Advancing shaft 115 through bore 116 and cavity 117 places a flange 115a at the distal end of shaft 115 into contact with side rail 90. Further advancement of shaft 115 exerts a clamping force against side rail 90 between flange 115a and the frame of coupler 106. When a sufficient clamping force is applied by shaft 115, relative movement between side rail 90 and coupler 106 is inhibited, and coupler 106 is placed in the locked state. While the above-described C-clamp provides an effective clamping mechanism, other types of clamps can also be used—e.g., a lever clamp, a spring clamp, a bar clamp, or the like. Similarly, other clamp cross-sectional shapes may be used, such as an inverted "J" in which the arc is placed over the side rail. Moreover, various other types of mechanisms suitable for transitioning coupler 106 between a locked and an unlocked state (cam, overcenter mechanism, wedge, etc.) can also be used without departing from the scope of the present disclosure.

Mounting device 104 further optionally includes ports 118 and 122. Port 118 is positioned near or on coupler 106, and port 122 is near or at the distal end of surgical arm interface 108. As discussed in more detail with reference to FIG. 5, ports 118 and 122 facilitate conveyance of a transportable medium to and/or from surgical arm 60. For example, ports 118 and 122 may enable transmission of electrical or optical control signals, electrical power signals (e.g., to operate arm 60, to apply electrosurgical energy to the patient, etc.), liquids (e.g., surgical irrigation or suction), gases (insufflation or suction), and so forth. In one example, port 118 receives the transportable medium from a source in the operating room and directs the medium to port 122 along a conduit (not shown) between the two ports. Upon receipt of the transportable medium, port 122 directs the medium to surgical arm 60. The conduit between ports 118 and 122 could extend through mounting device 104 or along the exterior of the device. In another example, the flow direction could be reversed, with port 122 receiving the medium from surgical arm 60 (e.g., fluid from the surgical site) and directing the medium along the conduit to port 118. In some examples, the mounting device could include two, three, or more sets of ports to facilitate conveyance of multiple different types of transportable mediums to and from the surgical arm during a surgical procedure.

Figure 4:
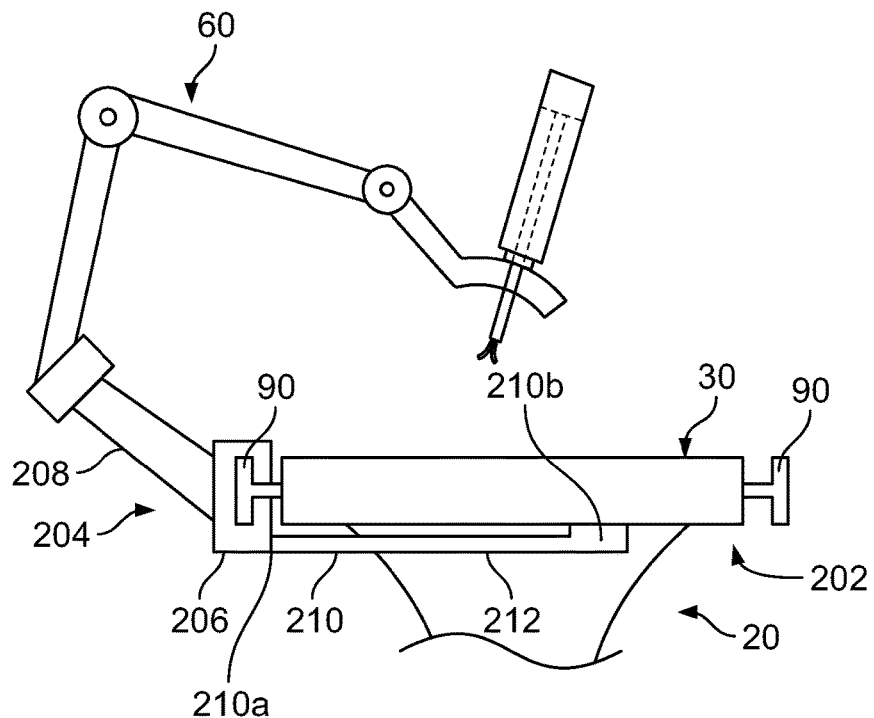
FIG. 4 is a front view of a second example mounting system.

FIG. 4 is a schematic view that depicts a second example surgical arm mounting system 202 that is similar to mounting system 102 described above with reference to FIGS. 1-3. In this example, mounting system 202 includes a single mounting device 204 removably secured to side rail 90 of operating table 20 by a coupler 206. Surgical arm 60 is mated to coupler 206 via a surgical arm interface 208. As in the previous example, mounting system 202 further includes a support member 210 to provide a rigid link between mounting device 204 and operating table 20. The rigid link in this example is provided by connecting a first end 210a of support member 210 to mounting device 204 and connecting a second end 210b of support member 210 directly to a portion of operating table 20 other than the opposite side rail. More specifically, the support member's second end 210b is connected to the underside of tabletop 30. Other attachment points to operating table 20 are also contemplated (e.g., an edge of tabletop 30, pillar 40, base 50, or the opposite side rail 90). Like the previous example, support member 210 includes a brace 212 between the two ends 210a,210b and that reinforces the operating table's side rail 90 in the manner described above. In some embodiments, support member 210's second end 210b rests securely against a portion of table 20 but is not secured to the table. In these embodiments, the additional support provided by brace 212 is sufficient to provide the additional stiffness between the surgical arm and the table. The brace may be rigid, or it may be spring-biased against the table at second end 210b.

Figure 5:
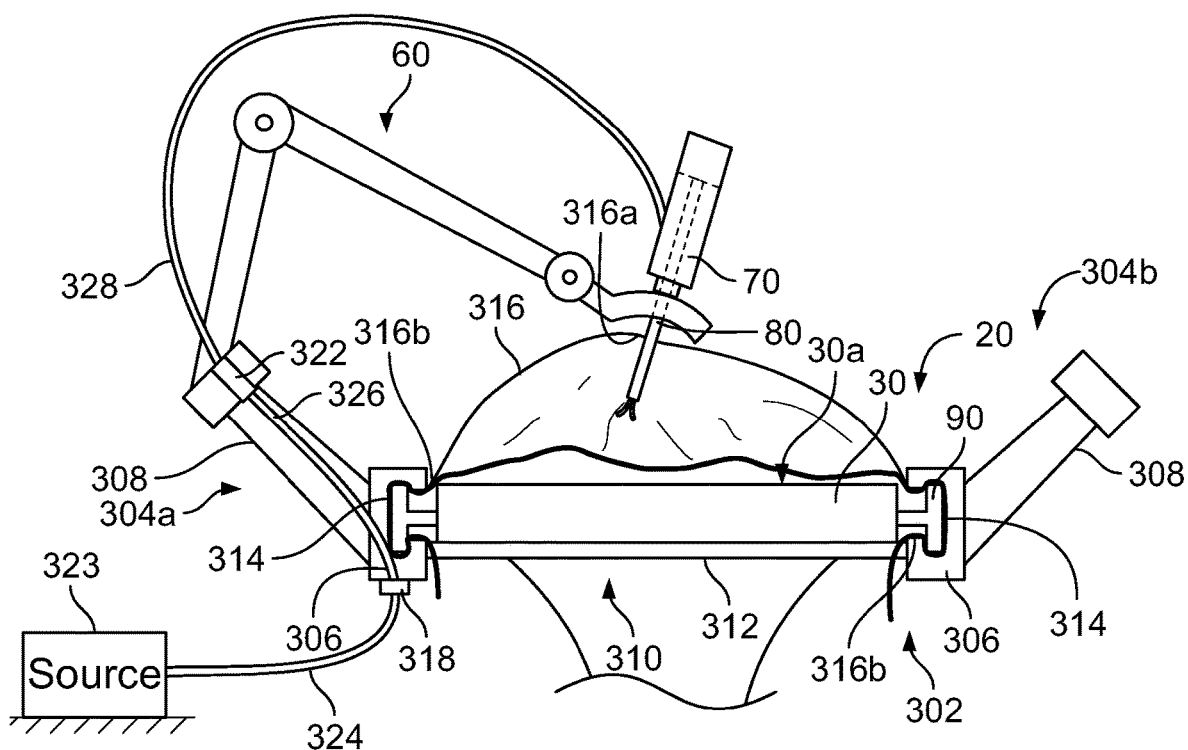
FIG. 5 is a front view of a third example mounting system.

FIG. 5 is a schematic view that depicts a third example mounting system 302 that is also similar to mounting system 102. Accordingly, mounting system 302 includes opposing mounting devices 304a,304b, each of which includes a coupler 306 securing the mounting device to the operating table's side rail 90. The mounting devices each also a surgical arm interface 308 for mating the surgical arm 60 to the mounting device. And as above, one of the surgical arm interfaces optionally may be omitted so that mounting system 302 is one-sided as illustrated by mounting system 202 in FIG. 4. A support member 310 includes a brace 312 extending between the two mounting devices 304a,304b to reinforce side rails 90 in the manner described above with reference to FIGS. 1-3.

The example of FIG. 5 demonstrates how mounting system 302 can be used to accommodate a sterile surgical drape 316. Surgical drape 316 may be made of a flexible, bag-like plastic (e.g., thermoplastic polyurethane) or any other flexible material capable of withstanding a sterilization process (e.g., cloth). As such, in some implementations, surgical drape 316 may be re-sterilized and so may be re-used over multiple surgical procedures. In other implementations, however, surgical drape 316 is sterilized for a single use (e.g., by gamma irradiation) and is thrown away after the surgical procedure.

As shown, drape 316 extends across tabletop 30 to cover the patient's body. Mounting devices 304a,304b are used to hold drape 316 in place, which prevents drape 316 from interfering with the movement of surgical arm 60. One side of drape 316 is placed over one side rail 90, and the opposite side of drape 316 is placed over the opposite side rail 90. The mounting device 304a,304b couplers 306 are placed over the drape and clamp to the side rails through drape 316. To move the arm position with reference to the table, the couplers are unlocked and translated over the drape to a new location on the side rails, at which the couplers are again clamped to the side rails through the drape. Alternatively, as described above, the couplers may be removed from the side rails and then re-clamped to the side rails through the drape at a new position. And although this through-the-drape clamping is described for two couplers, a similar situation exists if the support system has only a single mounting device, as illustrated by FIG. 4.

Drape 316 may be further held in place at or near the location at which the surgical instrument enters the patient. To hold drape 316 in place, for example, a proximal portion 316a is coupled to surgical arm 60 and opposing distal portions 316b are coupled to mounting devices 304a,304b. As one example, the drape's proximal portion 316a may include a cannula coupler (not shown) in the form of an internally threaded screw-on adapter that releasably engages a corresponding pattern of external threads formed on a cannula through which the surgical instrument enters. Alternatively, adhesives or other types of mechanical fasteners are used.

In some examples, the drape's distal portions 316b optionally include an adhesive on an inner side of drape 316 to facilitate attachment of distal portions 316b to the operating table's side rails 90. Distal portions 316b may be attached to side rails 90 before installing or positioning mounting devices 304a,304b. For instance, a distal portion 316b of drape 316 may be firmly attached to side rail 90 by the adhesive, closely overlaying the contour of side rail 90 to allow coupler 306 to slide along side rail 90 over drape 316. This arrangement enables movement of mounting device 304 while surgical drape 316 remains in a fixed position on the side rail so that translation is made easier with the drape bunching. Alternatively, adhesive is used to attach the drape's distal portion 316b to coupler 306, which would cause drape 316 to move together with mounting device 304 along side rail 90.

Still referring to FIG. 5, mounting device 304 is shown connected to a source 323 of a transportable medium—e.g., electrical or optical control signals, electrical power signals, liquids, or gases. As previously discussed with reference to FIG. 3, mounting device 304 includes ports 318 and 322 for conveying the transportable medium from source 323 in the operating room to surgical arm 60. In this example, the transportable medium is conveyed from source 323 to port 318 via conduit 324, from port 318 to port 322 via conduit 326, and from port 322 to surgical arm 60 via conduit 328. Conduits 326,328 are optionally internal or external to their associated components. In various implementations, the direction of flow is reversed to convey a transportable medium from surgical arm 60 to a discharge reservoir (not shown; similarly positioned to source 323).

FIG. 5 illustrates that port 318 may be positioned to be outside of a defined sterile surgical field (e.g., below the top surface 30a of tabletop 30) and port 322 may be positioned to be inside a defined sterile surgical field (e.g., above top surface 30a). In this way the outer surface of conduit 324 can be non-sterile while conduits 326,328 remain sterile.

Figure 6A:
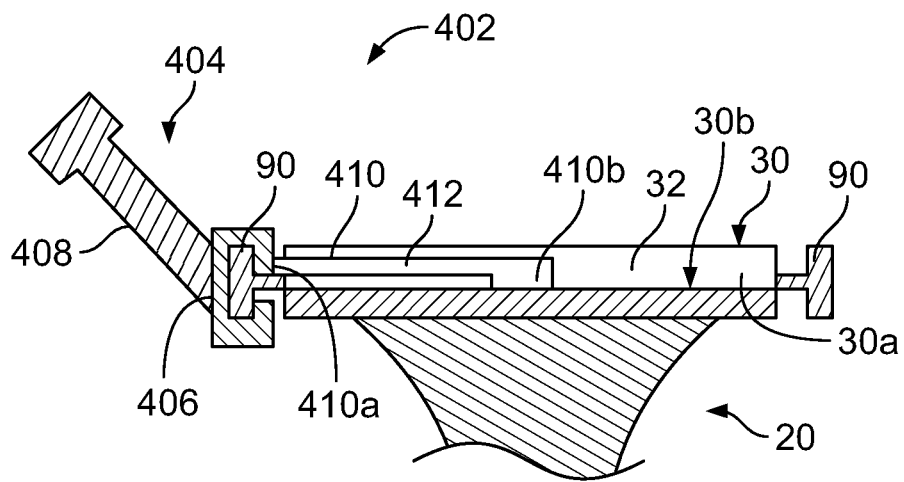
FIG. 6A is a front, cross-sectional view of the mounting system of FIG. 6, taken along the line 6A-6A in FIG. 6.
Figure 6:
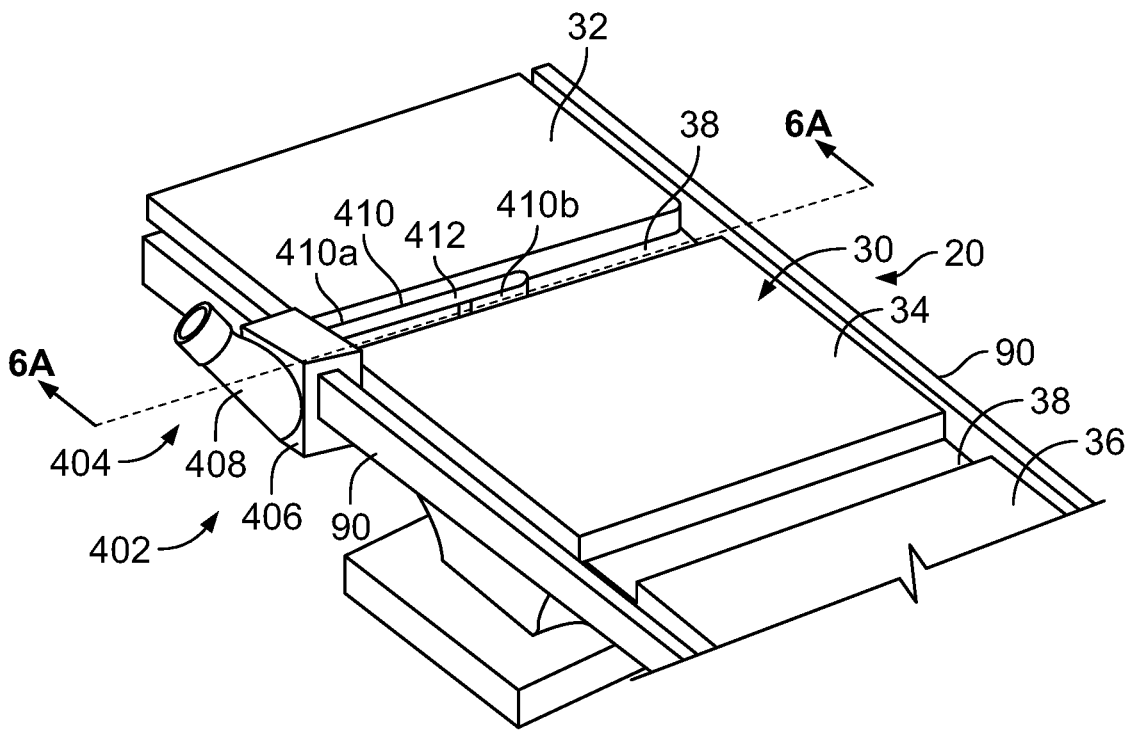
FIG. 6 is a perspective view of a fourth example mounting system.

FIGS. 6 and 6A depict a fourth example mounting system 402 that is similar to the second example mounting system 202 described with reference to FIG. 4. Accordingly, mounting system 402 includes a single mounting device 404. Mounting device 404 includes a coupler 406 that releasably secures the mounting device to one of the operating table's side rails 90 and a surgical arm interface 408 designed to mate with a surgical arm (e.g., surgical arm 60). A support member 410 including a brace 412 extends from a first end 410a connected to mounting device 404 to a second end 410b part way across tabletop 30. In some implementations brace 412 extends between tabletop top surface 30a and tabletop subsurface 30b. Alternatively, if no cushion is present, or if there are breaks between adjacent cushions, brace 412 extends across the tabletop immediately beneath the patient. Accordingly, although end 410b is shown projecting slightly downward, it may be part of a broad, flat monolithic brace under the patient.

In this schematic illustration tabletop 30 includes three independently adjustable sections—a headrest section 32, an upper body section 34, and a lower body section 36. Intermediate joints 38 facilitate relative pivoting movement between the respective tabletop sections 32,34,36 to provide an articulating surface for supporting the patient's body in various positions. In this example, the support member's second end 410b projects into a space between the adjacent cushions of headrest section 32 and upper body section 34 of tabletop 30. As shown, the low profile of support member 410 is such that the entire support member remains below a top plane of the adjacent tabletop sections 32,34, which prevents contact between support member 410 and the patient's body. Other configurations in which portions of the support member extend above the tabletop are also contemplated (see e.g. FIGS. 1-3). For example, in some implementations the brace is a broad, flat plate that rests atop the operating table, and the patient's body rests on the brace (or on a cloth that covers the brace) rather than the tabletop (see e.g., FIG. 8).

Figure 7:
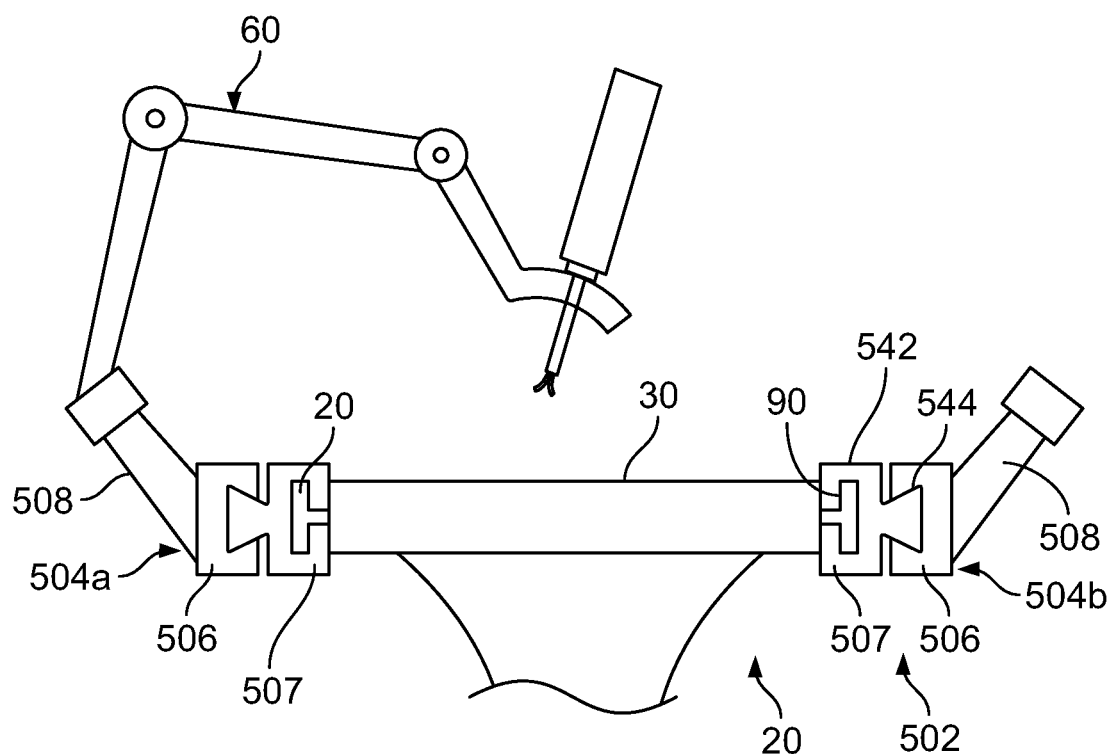
FIG. 7 is a front view of a fifth example mounting system.

FIG. 7 depicts a fifth example mounting system 502. Similar to prior examples, mounting system 502 includes opposing mounting devices 504a,504b, each of which includes a coupler 506 and a surgical arm interface 508 that mates the device to surgical arm 60. In this example, mounting system 502 further includes two auxiliary rails 507 installed to reinforce side rails 90 of operating table 20. Each of auxiliary rails 507 includes a frame 542 and a flange 544 extending outward from a rear surface of frame 542. Frame 542 has a "C"-shaped' cross section that defines an interior cavity for receiving side rail 90. These mating cross-sectional shapes enable installation by sliding an auxiliary rail 507 onto a side rail 90 from one end of operating table 20 towards the other. Alternatively, an auxiliary rail may be removably secured to a table side rail in a manner similar to the way a mounting device is coupled to a side rail as described above. A mounting device 504 is secured to an auxiliary rail flange 544 via coupler 506 using the same technique as described above with respect to the operating table's side rails 90.

Auxiliary rails 507 are configured (e.g., in terms of geometry and material) to provide a mounting point for supporting mounting devices 504a,504b and surgical arm 60 with increased stability compared to side rails 90. As previously discussed, stability in this context may be improved by increasing the strength of the mounting point to increase the stiffness of the mounting point to reduce vibration caused by static and dynamic load-induced deflection. For example, auxiliary rails 507 may be thicker and more robust than side rails 90, as is illustrated by FIG. 7, and therefore they provide increased stiffness and strength. As another example, the contour of auxiliary rails 507 may be shaped in a manner that reduces stress concentrations (e.g., rounded as opposed sharp corners) at the mounting points. As yet another example, the material selected for auxiliary rails 507 may have intrinsically greater strength and rigidity properties and/or the material may be treated in a manner that enhances these properties. As a further advantage, a single auxiliary rail can be configured to mount to several different operating table side rails, while the mounting flange is standardized to a single coupling device configuration. This design allows the coupling device associated with each arm to be simplified because it does not have to work with different side rail geometries, thus lowering cost.

Moreover, in this example, the shape and size of the auxiliary rail's frame 542 produces a buttressing effect by bracing side rail 90 against the side of tabletop 30. As shown, when auxiliary rail 507 is installed, the front side of its frame 542 abuts (or nearly abuts) tabletop 30. This arrangement causes tabletop 30 to exert a reactionary force against frame 542 that resists bending/twisting of side rail 90 induced by the load of surgical arm 60. In other words, the load of surgical arm 60 exerts a bending moment urging side rail 90 to deflect downward, and this deflection is prevented by the interaction between frame 542 and tabletop 30.

Two auxiliary rails are shown, but in some implementations only a single auxiliary rail is mounted to the table. As described below, if two auxiliary rails are used, as an alternative or in addition to the buttressing configuration, they may be coupled together as described above for the coupling devices. Alternatively, one or more single auxiliary rails may be coupled to a brace that extends part way across the tabletop in manner similar to the support systems illustrated in FIGS. 4 and 6. In this way, an auxiliary rail can be made more stiff and robust than its associated side rail.

Figure 8:
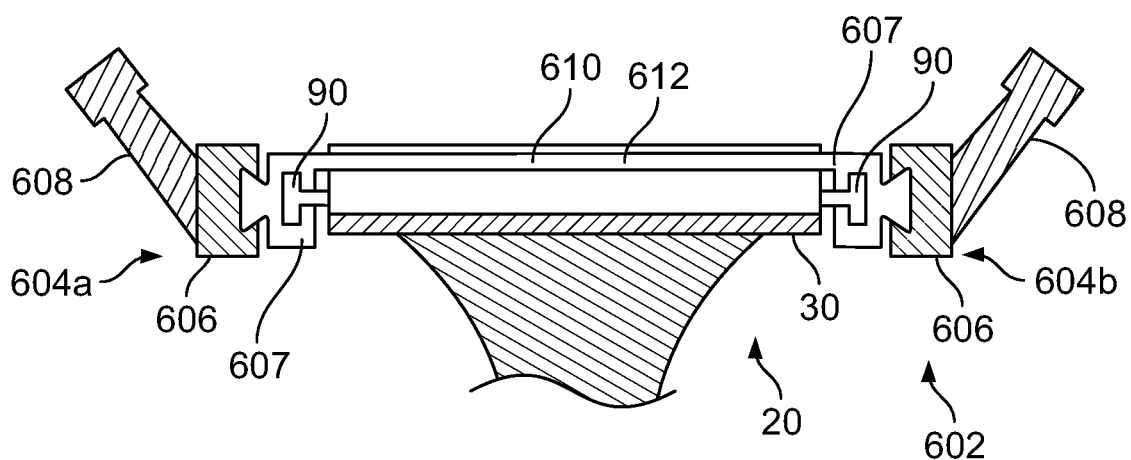
FIG. 8 is a front, cross-sectional view of a sixth example mounting system.

FIG. 8 is a cross-sectional schematic view that depicts a sixth mounting system 602 that is similar to mounting system 502 of FIG. 7. Accordingly, mounting system 602 includes opposing mounting devices 604a,604b, each of which includes a coupler 606 and a surgical arm interface 608 that mates the coupling device to a surgical arm (e.g., surgical arm 60). Like the previous example, mounting system 602 further includes two auxiliary rails 607 installed to reinforce side rails 90 of operating table 20. Auxiliary rails 607 provide a mounting point for supporting mounting devices 604a,604b. Mounting system 602 further includes a support member 610 including a brace 612 extending between auxiliary rails 607 that further reinforces the operating table's side rails 90 in the manner described above with reference to FIGS. 1-3. Brace 612 is provided in the form of a broad, flat structure that rests atop the operating table's tabletop 30, such that the patient's body rests on brace 612 during a surgical procedure. Like the similar embodiments described above, one advantage of this configuration is that the weight of the patient's body can further buttress brace 612 to provide additional reinforcement to the operating table's side rails 90 and the one or more auxiliary rails 607.

In this example, support member 610 is provided as an assembled modular unit with auxiliary rails 607, such that rails 607 and support member 610 can be installed simultaneously by sliding the entire module onto operating table 20. Various other table-mounting configurations such as those described above are also contemplated within the scope of this disclosure.

While a number of examples and aspects have been described for illustration purposes, the foregoing description is not intended to limit the scope of the invention, which is defined by the scope of the appended claims. There are and will be other examples and modifications within the scope of the following claims. For example, the system of ports and conduits for conveying transportable mediums to and from the surgical arm is described above with respect to the mounting devices, but these features can also be applied to the auxiliary rails. Similarly, while the embodiments described above are directed to the mounting of a surgical arm to an operating table, these techniques can be used to mount a surgical arm to virtually any structure in an operating room (e.g., wheeled or stationary surgical carts). As another example, the auxiliary side rails and mounting devices could be formed as a modular unit, with each side rail carrying multiple permanently attached mounting devices to provide different mounting locations. In such an implementation, the mounting devices may or may not include a coupler, and the surgical arm interface could be attached directly to the auxiliary rail.

What is claimed is:

1. A medical device system comprising:
   a surgical arm mounting device comprising:
     a coupler supported on a first rail; and
     a surgical arm interface projecting from the coupler to a distal end spaced apart from the first rail,
   a surgical arm attached to the surgical arm interface;
   wherein the surgical arm interface, the coupler, and the surgical arm are assembled to move together as a unit on the first rail; and
   a support member comprising a brace, wherein the brace extends at least part way across the width of an operating table;
   wherein the coupler has a first mechanical state in which the unit is fixed to the first rail, a second mechanical state in which the unit is translatable along the first rail while remaining attached to the first rail, and a third mechanical state in which the unit is removable from the first rail.

2. The system of claim 1, further comprising:
   a second mounting device comprising a second coupler, for a second rail opposite the first rail.

3. The system of claim 2, wherein the second coupler has a first mechanical state in which the second mounting device is fixed to the second rail, a second mechanical state in which the second mounting device is translatable along the second rail, and a third mechanical state in which the second mounting device is removable from the second rail.

4. The system of claim 3, wherein the second mounting device comprises a second surgical arm interface; wherein the second surgical arm interface is configured to receive the surgical arm.

5. The system of claim 1, wherein in the first mechanical state the coupler is fixed to the first rail through a surgical drape; and wherein in the second mechanical state the coupler is translatable along the first rail over the surgical drape.

6. The system of claim 1, wherein the brace extends over a top surface of an operating table, and wherein the brace is coupled to the mounting device.

7. The system of claim 6, wherein the brace comprises a broad, flat body.

8. The system of claim 1, wherein the brace extends underneath the operating table.

9. The system of claim 1, wherein the mounting device further comprises first and second ports for a transportable medium and a conduit for the transportable medium extending between the first and second ports.

10. The system of claim 9, wherein the conduit extends from the first port to the second port through the interior of the mounting device.

11. The system of claim 9, wherein the conduit comprises at least one of a fluid conduit or an electrical conduit.

12. The system of claim 1, further comprising an operating table.

13. The system of claim 1, further comprising a surgical drape between the first rail and the coupler.

14. A teleoperated surgical arm mounting system comprising:
   means for releasably coupling to a first side rail of an operating table;
   means for bracing the means for releasably coupling against a second part of the operating table; and
   means for mating a teleoperated surgical arm to the means for releasably coupling.

15. The system of claim 14, wherein the second part of the operating table comprises a second side rail on an opposite side of the operating table.

16. The system of claim 14, wherein the second part of the operating table comprises the bottom of the table.

17. The system of claim 14, wherein the second part of the operating table comprises the top of the table.

18. The system of claim 14, wherein the second part of the operating table comprises a side of the table.

19. The system of claim 14, where the means for releasably coupling comprises means for releasably coupling over a surgical drape covering the first side rail.

* * * * *